United States Patent [19]
Hüskens et al.

[11] Patent Number: 5,836,768
[45] Date of Patent: Nov. 17, 1998

[54] FASTENING DEVICE FOR FIXING ORTHODONTIC APPARATUSES ON A DENTAL IMPLANT

[75] Inventors: Christoph Hüskens, Horn; Ulrich Mundwiler, Tenniken, both of Switzerland; Jürgen Glatzmaier, Munich, Germany

[73] Assignee: Institut Straumann AG, Waldenburg, Switzerland

[21] Appl. No.: 860,331

[22] PCT Filed: Dec. 22, 1995

[86] PCT No.: PCT/CH95/00303

§ 371 Date: Sep. 2, 1997

§ 102(e) Date: Sep. 2, 1997

[87] PCT Pub. No.: WO96/19946

PCT Pub. Date: Jul. 4, 1996

[30] Foreign Application Priority Data

Dec. 23, 1994 [CH] Switzerland ............... 3921/94

[51] Int. Cl.⁶ .................................................. A61C 8/00
[52] U.S. Cl. .............................. 433/173; 433/8; 433/24; 433/172
[58] Field of Search ........................ 433/8, 9, 24, 172, 433/173

[56] References Cited

U.S. PATENT DOCUMENTS

| 4,988,292 | 1/1991 | Rosen | 433/8 |
| 5,015,186 | 5/1991 | Detsch | 433/8 |
| 5,071,345 | 12/1991 | Rosen | 433/24 |
| 5,082,442 | 1/1992 | Rosen | 433/24 |
| 5,205,745 | 4/1993 | Kamiya et al. | 433/173 |
| 5,232,364 | 8/1993 | Rosen | 433/8 |

FOREIGN PATENT DOCUMENTS 9612451 2/1996 WIPO.

*Primary Examiner*—John J. Wilson
*Attorney, Agent, or Firm*—Selitto & Associates

[57] ABSTRACT

For a dental implant (10) which can be inserted into the jaw bone (1) and which is intended principally as a support for a crown or another superstructure, an anchoring base (30) which s can be fitted releasably on the implant (10) was created for the purpose of preliminary orthodontic treatment. The vertical outer sides of the anchoring base (30) are designed as fastening surfaces (31). A bracket (50) can be fixed on a selected fastening surface (31) by means of a bonding layer (60). Orthodontic apparatus components (70, 71) are fastened on this bracket (50). The anchoring base (30) is screwed onto the implant (10) using an occlusal screw (80) and in the process can be locked in a finely adjustable position of rotation. The eccentrically arranged bore (37) promotes adaptation to the spatial conditions and to the orthodontic task. The anchoring base (30) is suitable for a wide range of types of implants (10) and brackets (50). Once the correction of the positioning of the teeth is complete, the anchoring base (30), which is made of titanium and is re-usable, can be removed in a simple manner from the implant (10). By means of the preferred adhesive bonding connection, galvanic corrosion between the stainless steel bracket (50) and the anchoring base (30) is substantially ruled out.

10 Claims, 3 Drawing Sheets

FASTENING DEVICE FOR FIXING ORTHODONTIC APPARATUSES ON A DENTAL IMPLANT

The invention relates to a fastening device on a single-piece or multi-piece dental implant, which is fitted in the jaw bone, for the fixing of orthodontic apparatuses and the subsequent use of the implant as a support for a crown or another superstructure, and with the implant head, or the transmucosal unit applied thereon, protruding from the soft tissue.

The purpose of orthodontic apparatuses is to correct congenital or acquired malpositioning of the teeth. Orthodontic is arch wires fastened on brackets are often used for moving the teeth which are in need of correction. The torsional and/or bending stress of such a wire is utilized as a means of exerting a force on the teeth which are to be moved. The wire extends between an attachment point, which is positioned in as stable a manner as possible, and the tooth which is to be corrected, or a group of teeth. The attachment point can either consist of a plurality of teeth taken together to form a block, or of an inserted implant. This invention concerns the latter alternative.

PRIOR ART

The brackets are either bonded directly onto the enamel of the teeth which are to be moved, using a suitable special adhesive, or else the brackets are soldered onto a closed metal band which is prepared from an impression and which is cemented firmly around the tooth. At one end, the orthodontic wire is fastened in this bracket, and, at the other end, the wire is supported on an implant. This implant could be an implant designed purely for orthodontic treatment, as is described in PCT patent application no. WO 96/12451. An implant of this type has a clamp cap which can be screwed on and fixed in any position and which has a peripheral guide slot for receiving the wire. After the positioning of the teeth has been corrected, this purely orthodontic implant is then removed. However, it is also possible to use, as the attachment point, implants which have a dual function, that is to say, in the first instance, of fixing an orthodontic wire, and, in the second instance, of acting as a support for a crown or another superstructure. In order to increase the force acting on the teeth which are to be moved, the arch wires are in most cases combined with traction or compression springs or with elastic bands.

The invention relates especially to a fastening device for fixing an orthodontic apparatus on a bifunctional dental implant. Hitherto, a provisional, individual or prefabricated crown has been applied on the implant when correction of a malpositioning of the teeth is first envisaged. A bracket for receiving the orthodontic wire is fastened on the temporary crown (see U.S. Pat. No. 5,232,364). This procedure has several drawbacks. A costly feature in the first place is that a provisional crown has to be fitted at all. Providing a bracket means that it subsequently has to be pulled off again, and in so doing each crown is damaged to the extent that it can no longer be used. When using a specific provisional crown, the subsequent choice of the wire shapes is restricted, since a wire joint of specific contour is often worked into crowns of this type. A trimming of the provisional crown is also ruled out because of the wire joints. In most cases, the dentist will also bond the bracket itself onto the provisional crown already in place in the mouth, and will not be able to fit a crown which has already been equipped with a bracket by the dental technician. As a consequence, the patient and the dentist are caused further inconvenience. The required readjustment of the apparatus located in the mouth of the patient necessitates considerable effort during ortho-dontic treatment. Finally, the provisional crown, which has been damaged by the bracket being pulled off after the malpositioning has been corrected, has to be removed in its entirety from the implant in order subsequently to apply the final crown or the intended superstructure onto the implant. All in all, this procedure entails considerable costs, and other conventional apparatuses are in some cases just as unsatisfactory because they are not corrosion-proof and are not anchored with sufficient stability, or else because they create a distinct feeling of there being an obstruction within the mouth. Only some improvement was achieved with the device according to U.S. Pat. No. 4,988,292. The anchoring base which is proposed in that document and which can be screwed onto the inserted dental implant is complicated in its design, offers little flexibility as regards the positioning possibilities, and is of only limited reliability.

OBJECT OF THE INVENTION

The invention is therefore based on the object of providing a more practical means of fastening an orthodontic apparatus on a bifunctional dental implant. A particular consideration here is to reduce the amount of work involved and the outlay in terms of material, and in so doing to minimize the costs and the inconvenience caused to the patient. The fastening device to be designed for fixing the orthodontic wire on the implant has to guarantee a stable anchoring, sufficient corrosion resistance and good biocompatibility so as to minimize the risk of the patient suffering allergic reactions. It is desirable that the fastening appliance should permit very variable, but readily adjustable settings, and that a large part of the work can be carried out in advance by the dental technician, away from the patient's mouth.

NATURE OF THE INVENTION

The principle of the invention lies in the fact that for a dental implant which can be fitted in a jaw bone primarily as a support for a crown or another superstructure, a dental apparatus component has been created in the form of an anchoring base which can be fixed on the implant. This anchoring base is used during preliminary orthodontic treatment by means of a bracket being attached to the anchoring base by adhesive bonding, soldering or welding, which bracket is used in turn for the fastening of apparatus components such as orthodontic wires or springs. In the anchoring base a through-bore provided for the passage of an occlusal screw is arranged eccentrically so that the anchoring base can be aligned in a variable manner depending on the interspace existing between the adjacent teeth, and on the orthodontically most favourable position. A still greater variability in terms of positioning is obtained with an anchoring base which can also be fixed upside-down on the implant.

With the fastening appliance according to the invention, a number of therapeutic, dental and financial advantages are obtained. The existing procedure is simplified for the patient, the dentist and the dental technician. Extensive preliminary work on adapting an anchoring base and fitting it with a bracket can be carried out by the dental technician under laboratory conditions, away from the patient's mouth. The negative effect of the moisture of the oral cavity on the quality of the customary adhesive connections is obviated, and the former problems of corrosion of the apparatus components are substantially reduced. The use of a crown which can be used only once, and which is then destroyed, as an attachment on the actual implant for orthodontic treatment is rendered unnecessary. By contrast, an anchoring base which has been used can be cleaned after use and then used once again. It is possible to trim and thus adapt the anchoring base frequently. Any necessary readjustment of the device can be effected in a relatively simple way. The transition from orthodontic therapy to the secondary use of the implant as a support for a crown or a superstructure has been made considerably simpler by reason of the uncomplicated removability of the anchoring base. Finally, the amount of work to be done by the dentist is reduced, and all the factors taken together have the result of cutting costs.

DRAWINGS AND EXEMPLARY EMBODIMENT

A detailed description of an exemplary embodiment of the fastening device according to the invention is given hereinbelow with reference to the attached drawings, and possible modifications are mentioned at the conclusion. In the drawings.

Figure 1:
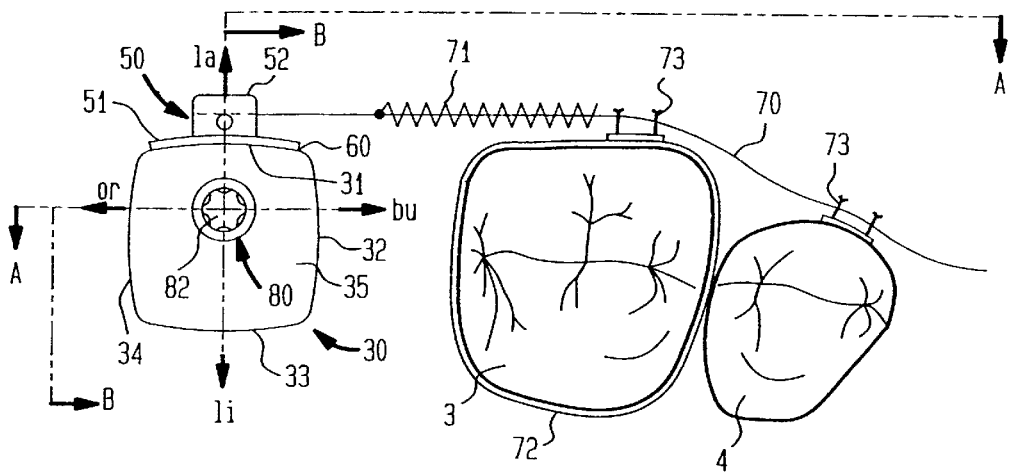
FIG. 1 shows a section of an upper or lower jaw, in a plan view, with the fastening device according to the invention on the dental implant, and with an orthodontic apparatus extending to the teeth.
Figure 2:
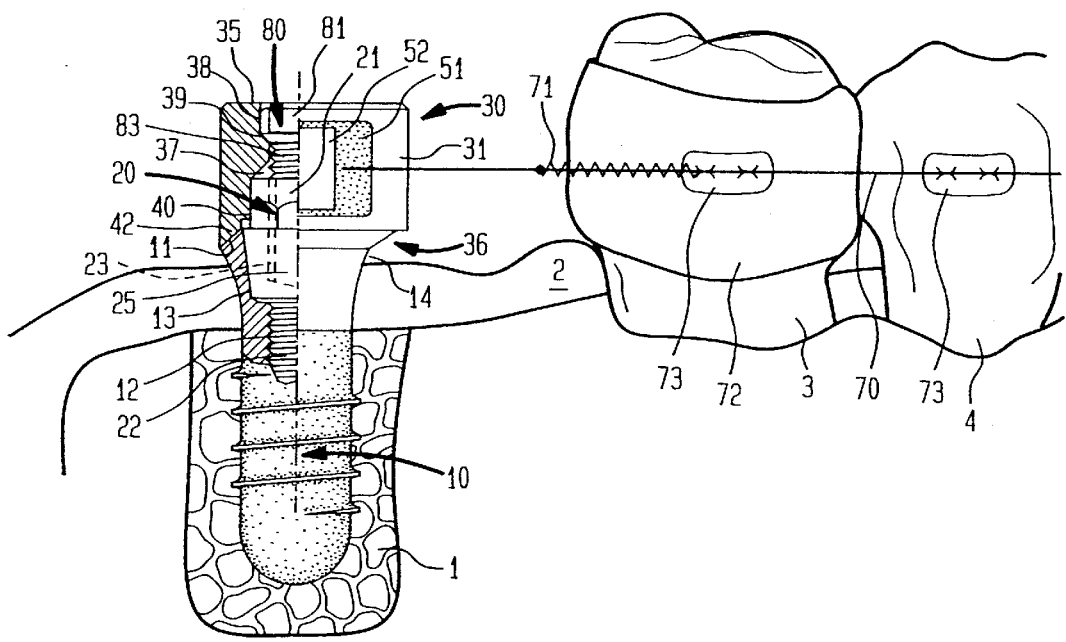
FIG. 2 shows the partial section along the line A—A in FIG. 1 (enlarged)
Figure 3:
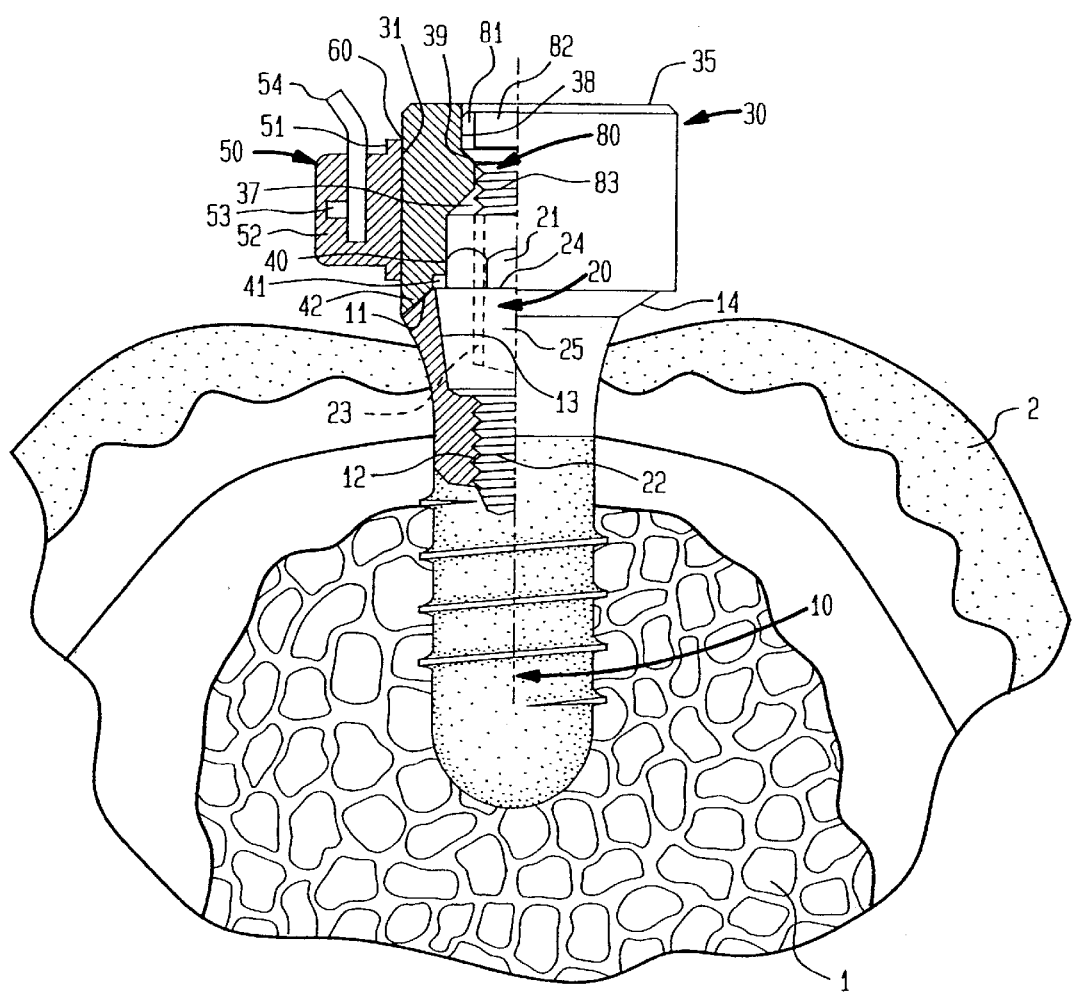
FIG. 3 shows the partial section through the implant screwed into the jaw bone, with the anchoring base screwed on in accordance with FIG. 1 along the line B—B (enlarged)

The following applies for the whole of the subsequent description. If, for the purpose of clarity of the drawings, reference numbers are included in a figure but are not explained in the directly relevant text in the description, then reference is made to their explanation in the description of the preceding figures. In the interests of clarity, the repeated identification of components in succeeding figures is in most cases dispensed with, as long as it can be clearly seen from the drawings that these are "recurring" components.
FIGS. 1 to 3

An implant 10 which is conventional per se—and which is in the form of a primary part—is inserted into a jaw bone 1, with the implant shoulder 11 lying over the soft tissue 2 which covers the jaw bone 1. A conventional anchoring screw 20—in the form of a secondary part—is screwed into the implant 10. The screw head 21 of the anchoring screw 20, designed as an octagon, protrudes above the implant shoulder 11, while the threaded part 22 of the anchoring screw 20 engages in an axially arranged threaded bore 12 in the implant 10, which threaded bore is in the form of a blind hole. The anchoring screw 20 for its part possesses a threaded bore 23 which is likewise in the form of a blind hole and which extends from the screw head 21 axially into the interior of the anchoring screw 20. Adjoining the octagonal screw head 21 of the anchoring screw 20 there is a screw cone 25 which has a wider diameter and which tapers conically downwards, so that an annular shoulder 24 is formed at the transition from the octagonal screw head 21 to the screw cone 25. The threaded part 22 extends further downwards from the screw cone 25 and tapers.

In the screwed-together state, the screw cone 25 sits in the internal cone 13 in the implant head 14. The annular shoulder 24 in this case protrudes—depending on tolerances—as far as approximately the level of the upper edge of the implant shoulder 11 Thus far, the functional elements which have been mentioned are known per se and are described and shown, for example, in the reference work by Schroeder/Sutter/ Buser/Krekeler: Orale Implantologie [Oral implantology], 2nd edition, Georg Thieme Verlag, Stuttgart—New York, 1994, pages 192 and 210.

Fitted onto the implant shoulder 11 is a basically parallelepipedal but rounded anchoring base 30, the centre-piece of the invention. The four convex outer surfaces which run vertically on a positioned anchoring base 30 are designated as fastening surfaces 31 to 34. A bracket 50 which is a standard one is bonded by means of a thin bonding layer 60 on one of the fastening surfaces, in this example on fastening surface 31. The bracket 50 is used, as shown here for example, for fixing an orthodontic wire 70 which guides a spring 71, with the spring 71 and the wire 70 extending as far as the tooth 3 which is to be moved. In accordance with the prior art, this tooth 3 has a metal band 72 wound around its circumference, on which metal band a bracket 73 is also fastened by adhesive bonding or by soldering. The wire 70 is mounted in the bracket 73 and, depending on the treatment plan, extends to further teeth 4 and is fixed there as well in brackets 73 which are arranged on these teeth.

With reference to FIG. 1, which is a plan view of the top surface 35 of the anchoring base 30, the horizontal cross-sectional surface of the later is in the form of a square which bulges out convexly on all sides. The bottom surface 36 lies opposite the top surface 35. For ease of understanding, the anchoring base 30 is placed in a theoretical graticule. Taking the example of the lower jaw, this could be the labial-lingual (1a-1i) and buccal-oral (bu-or) axes.

Lying at the eccentric point of intersection of these axes is the bore 37 which runs vertically through the anchoring base 30 and which is used for receiving a conventional occlusal screw 80 which is introduced from above. The occlusal screw 80 has the screw head 81 with the nonrotationally symmetrical engagement contour 82 which is located at the upper side for the engagement of a corresponding screwing instrument, and the threaded shank 63 of reduced diameter.

Starting from the top surface 35, the bore 37 first has a head portion 28 and, lying below the latter, a narrowed screw seat 39. The screw head 81 can be lowered in the head portion 38 and bears on the screw seat 39. Below the screw seat 39, the bore 37 widens again and is designed as an icositetrahedron 40. Provided at the lower end of the icositetrahedron 40 is a radially circumferential, widened groove 41. Should the annular shoulder 24 on the anchoring screw 20 rise above the implant shoulder 11 as a result of tolerances at the insertion depth, it penetrates into the free space of the groove 41 and does not have a disruptive effect.

Adjoining the groove 41 is the counter-shoulder 42 which opens out at the bottom surface 36 and which widens conically downwards as a circular ring surface and is designed to complement the implant shoulder 11. As a result of the eccentricity of the bore 37, the counter-shoulder 42 lies near the fastening surface 31.

The anchoring base 30 is pressed firmly onto the implant 10 by means of the occlusal screw 80; the counter-shoulder 42 sits on the implant shoulder 11 practically without any gap. The octagon of the screw head 21 engages with a positive fit in the icositetrahedron 40 in the anchoring base 30.

As a result of the positive fit between the octagon of the screw head 21 and the icositetrahedron 40, it is possible in principle to fix the anchoring base 30 on the implant 10 in 24 different positions of rotation, each at 15° stages. With the bore 37 arranged eccentrically, four different alternative positions, each offset by 90°, can be set at each angular position selected. This means, for example, that four different distances can be set in the labial direction between the bore 37 and the fastening surface in question—in this case 31. If the distance in the labial direction is the determining one, and if this was established by positioning of the corresponding fastening surface 31, then the distances in the buccal, lingual and oral directions are obtained automatically. If one were to turn the anchoring base 30 through 180°, then the fastening surface 33 would lie to the front, as a result of which a greater distance would be obtained from the bore 37 to the now frontal fastening surface 33. The distances from the bore 37 to the adhesion fastening 34, 32 in the buccal and oral directions have changed round. A high degree of adaptability of the fastening device to the respective dental situation and task and also to the spatial conditions in the area surrounding the fitted implant 10 has been achieved in this way. An optimal guide angle for the orthodontic wire 70 is possible.

The bracket 50 is bonded adhesively with its support plate 51 onto the fastening surface 31. The previously applied thin bonding layer 60 provides for reliable adhesion. The adhesive connection is established using a method which is conventional to the person skilled in the art. All suitable adhesives may be considered as the bonding substance, for example Panavia® from the company Cavex Holland B.V., a composite-based cement possessing the required chemical and mechanical retention, on metals too, and with sufficient adhesiveness.

Provided on the back of the support plate 51 of the bracket 50 are, depending on the type in question, clamping eyelets, suspension hoops or bars for fixing the orthodontic wire 70 or other orthodontic means such as springs or rubber bands. In FIG. 3, for example, a bracket 50 is fitted with its support plate 51, on the back of which there is provided a clamping eyelet 52 with a through-opening 53 and a bar 54. The orthodontic wire 70 is threaded through the through-opening 53 and is clamped by a twisting of the bar 54.

Because of its excellent biocompatibility, unalloyed titanium has proven effective as an implant material. For the anchoring base 20 joined together directly with the implant 10, a material was to be chosen which is not far removed galvanically from the implant material in order to avoid crevice corrosion, which can cause bacterial growth and resulting inflammations. It is therefore of advantage for the anchoring base 30 likewise to be made of unalloyed or alloyed titanium. By contrast, the attached brackets 50 usually consist of stainless steel, which in turn has a sufficient strength and corrosion resistance. Ceramic or titanium are also used, inter alia, for the brackets 50. The bonding layer 60 interposed when sticking the support plate 51 of the bracket 50 onto one of the fastening surfaces 31 to 34 of the anchoring base 30 acts as an electrically insulating layer between the materials of differing galvanic potential, so that corrosion is ruled out at the material transitions, or, in the event of a microscopically incomplete bonding layer 60, is at least admissibly slight.

For the adhesiveness of the adhesive connection, it has proven advantageous to give the fastening surfaces 31 to 34 a surface roughness in the region of roughness grades N10 to is N12, with a mean roughness value of $R_a$ from 12.5 mm to 50.0 mm. A particularly good adhesiveness of the bonding substance is obtained by silanization of the fastening surfaces 31 to 34 of the anchoring base 30 and the adhesion surfaces on the support plates 51 of the brackets 50.

Figure 4:
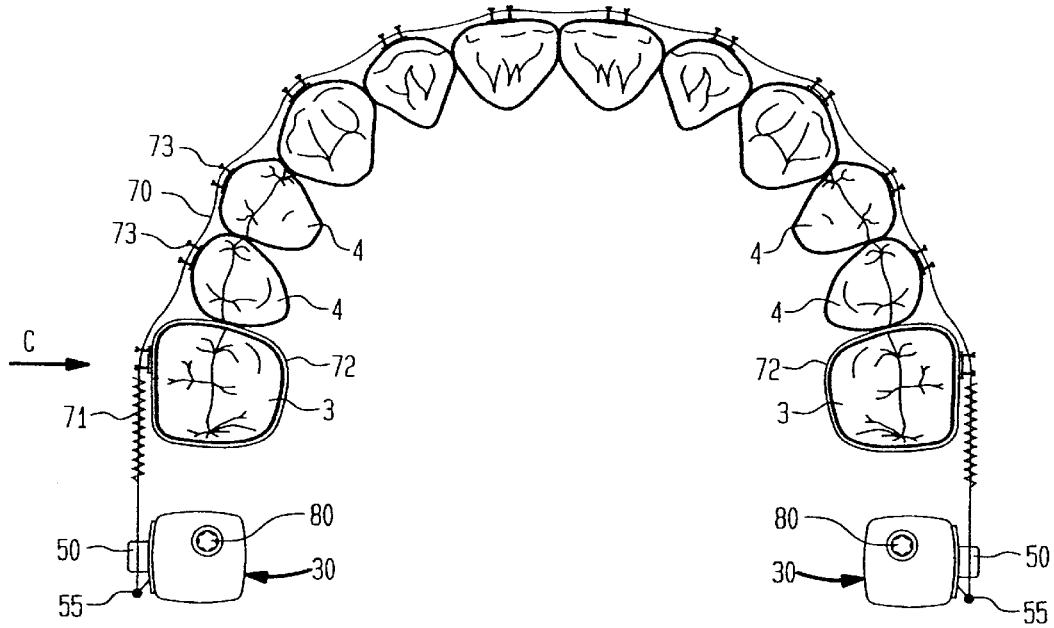
FIG. 4 shows an upper or lower jaw in plan view, with implants screwed in on both sides in the retromolar area, and with an orthodontic apparatus secured thereon.
Figure 5:
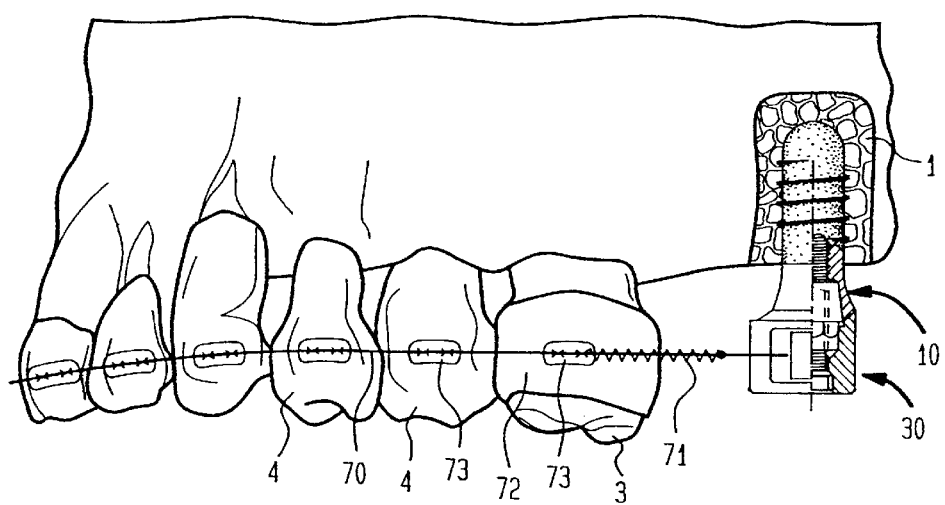
FIG. 5 shows a cutaway view of the upper jaw in accordance with FIG. 4 in the viewing direction C.

FIGS. 4 and 5

These figures illustrate an example of an orthodontic apparatus for correcting the position of the teeth using the fastening appliance according to the invention. Continuously acting forces are exerted by the apparatus on the teeth 3, 4 which are to be moved. An implant 10 introduced into the lower or upper jaw, in this case on both sides, by a conventional method is used as a stable anchoring element. The implant head 14 is sealed off during the period of incorporation. Following the period of incorporation, the seal is removed and an anchoring screw is screwed in, and the anchoring base 30, which has been provided with a bonded-on bracket 50, possibly in advance outside the oral cavity, is then attached and is oriented according to the relevant conditions. The anchoring base 30 is then fixed on the implant 10 by means of an occlusal screw 80. If necessary, a prefabricated metal band 72 with an attached bracket 73 is in practice placed radially around the adjacent molar 3, and further teeth 4 in the mesial direction are provided with brackets 73. Finally, the orthodontic wire 70 is guided into the brackets 50, 73, which wire 70 can be equipped with further apparatus components, in this case springs 71, and the wire 70 is fixed, in the end-position brackets 50, on the parts provided for this purpose, for example a suspension loop 55. The orthodontic wire 70 stretches tight from one anchoring base 30, which is fitted on an end-position implant 10, and around an entire row of teeth as far as a second such anchoring base 30.

The following possible modifications to the fastening device as described thus far may be given special mention:

Instead of on a single-part implant 10 whose head 14 protrudes from the soft tissue 2, the anchoring base 30 can also be fitted on a transmucosal unit of a multi-part implant.

The anchoring base 30 is constructed in various sizes, in particular heights. If the bore 37 has been arranged centrically rather than eccentrically, the necessary geometrical adaptations can also be achieved by trimming of the anchoring base 30.

As regards the horizontal cross-sectional shape, a basically rectangular or triangular anchoring base 30 with outwardly bulged, convex fastening surfaces 31 to 34 and rounded corners could also be given consideration. Such an anchoring base 30 could be provided with respectively, four or three different surface curvatures for correctly receiving respective brackets 50. Oval or circular shapes are also conceivable, in which case there are no longer any mutually delimited fastening surfaces.

The chosen number of edges on the screw head 21 of the anchoring screw 20 and on the inner edge 40 in the anchoring base 30 can be varied insofar as a useful functioning is achieved. The positions of rotation which can be fixed between implant 10 and anchoring base 30 could also be made possible by a polygon protruding from the anchoring base 30 and engaging in an internal polygon in the implant 10.

The bonding layer 60 can also represent, in addition to the preferred adhesive connection, a soldering or welding connection.

If only one fastening surface is provided on an anchoring base 30, it can be advantageous to arrange a raised, protruding material ridge on this fastening surface, near the bottom surface 36. This material ridge can be produced by means of material being removed to some extent from the fastening surface as far as the level of the upper edge of the material ridge. A bracket 50 which is fixed on this fastening surface protrudes to a lesser extent and thus interferes to a lesser extent in the oral cavity.

The counter-shoulder 42 on the anchoring base 30 does not need to have the previously described conical shape. The shape of the counter-shoulder 42 is dependent on the shape of the implant shoulder 11.

If a counter-shoulder 42 is configured in each case on the top surface 35 and on the bottom surface 36, and if an internal polygon 40 is provided both above and below a screw seat 39 which can be used bilaterally, then the anchoring base 30 can also be screwed upside down onto the implant 10. When the bore 37 is arranged eccentrically, there are then four further possibilities as regards the positioning of the anchoring base 30, i.e. in the distribution of the various distances from the bore 37 to the respective fastening surface 31 to 34.

The internal polygon 40 in the anchoring base 30 is not compulsory. When using an anchoring screw 20 with a cylindrical or conical screw head 21, the rotational securing of the anchoring base must be effected either by the tightening of the occlusal screw 80 alone, and the resulting surface contact pressure, or else by additional means.

where there are special aesthetic requirements, primarily in the labial region, the implant could be inserted deeper within the bone, and thus the lower portion of the anchoring base 30 could be surrounded at least to some extent by the gingiva.

We claim:

1. Fastening device on a dental implant for the fixing of orthodontic apparatus components and the subsequent use of the implant, fitted in the jaw bone and having an implant shoulder, as a support for a superstructure, in which:
   a) the implant head protruding at least to some extent from the soft tissue, and
   b) an anchoring base which can be fitted on the implant shoulder of the implant is provided with at least one fastening surface, and
   c) this fastening surface serves for fastening of a support plate of a bracket, and
   d) at least one apparatus component can be fixed on the bracket, and
   e) the anchoring base has a vertically continuous bore, and
   f) the anchoring base can be fixed on the implant by means of an occlusal screw which is guided through the bore and which engages into the implant, and
   g) polygons of male and female configuration, respectively, are alternatingly present on the implant and on the anchoring base and engage with one another with positive locking, so that the anchoring base can be placed on the implant in various stable positions of rotation, characterized in that,
   h) the bore is eccentrically provided in such a way that different distances from the bore to the fastening surfaces are obtained in a gradation.

2. Fastening device according to claim 1, characterized in that
   a) an anchoring screw is provided which can be screwed into the implant head, and
   b) the screw head of the screwed-in anchoring screw protrudes from the implant head and is designed as a polygon, and
   c) a threaded bore extends from the screw head into the anchoring screw, and
   d) the bore in the anchoring base has at least one section with an internal polygon, and
   e) the polygon on the screw head engages with positive locking in the internal polygon, and
   f) in the assembled state, the occlusal screw rests with its screw head on a screw seat located in the bore, while its threaded shank engages in the threaded bore of the anchoring screw.

3. Fastening device according to claim 2, characterized in that
   a) the screw seat can be used both for an occlusal screw which has been introduced into the bore from the top surface and also for an occlusal screw which has been introduced into the bore from the bottom surface, and
   b) within the bore, on both sides, and adjoining the screw seat, there is in each case a section with an internal polygon, and
   c) the screw head finds room in that section of the internal polygon which is not used to complement the outer polygon of the screw head, and on the outside the bore opens out in each case with a counter-shoulder which complements the implant shoulder.

4. Fastening device according to claim 3, characterized in that the screw head is designed as an octagon and the inner edge as an icositetrahedron, so that a rotational positioning of the anchoring base is possible in 15° stages.

5. Fastening device according to claim 3, characterized in that the counter-shoulder opens outwardly conical complementary to the implant shoulder.

6. Fastening device according to claim 1, characterized in that
   a) the anchoring base has in principle the shape of a parallelepiped whose four vertical side surfaces form the fastening surfaces which bulge convexly outwards, and
   b) the fastening surfaces can have different radii of curvature, at least in pairs.

7. Fastening device according to claim 1, characterized in that
   a) the implant and the anchoring base are made of titanium, and
   b) the brackets which are to be applied on the anchoring base are made of a material selected from the group consisting of stainless steel, ceramic and titanium, and
   c) the fastening surfaces provided on the anchoring base have a surface roughness in the region of roughness grades N10 to N12, with a mean roughness value in the range 12.5 $\mu$m<$R_a$<50.0 $\mu$m, and
   d) at least the fastening surfaces on the anchoring base and the adhesion surface on the support plate are silanized.

8. Fastening device according to claim 1, characterized in that the support plate of he bracket is fixed on the fastening surface by means of a bonding layer wherein the bonding layer represents an adhesive.

9. Fastening device according to claim 1, characterized in that the support plate the bracket is fixed on the fastening surface by means of a bonding layer wherein the bonding layer represents a soldering.

10. Fastening device according to claim 1, characterized in that the support plate of he bracket is fixed on the fastening surface by means of a bonding layer wherein the bonding layer represents a welding.

* * * * *